United States Patent [19]
Morré et al.

[11] Patent Number: 5,569,673
[45] Date of Patent: Oct. 29, 1996

[54] CAPSACINOID COMPOUNDS AS PROLIFERATION INHIBITORS

[75] Inventors: D. James Morré; Dorothy M. Morré, both of West Lafayette, Ind.

[73] Assignee: Purdue Research Foundation, West Lafayett, Ind.

[21] Appl. No.: 248,084

[22] Filed: May 24, 1994

[51] Int. Cl.$^6$ .......................... A01N 37/34; A61K 31/275
[52] U.S. Cl. .......................................................... 514/522
[58] Field of Search ............................................. 514/522

[56] References Cited

U.S. PATENT DOCUMENTS 5,001,115   3/1991   Sloan ........................................ 514/34

OTHER PUBLICATIONS

Bruno et al., "Stimulation of NADH Oxidase Activity from Rat Liver Plasma Membranes by Growth Factors and Hormones is Decreased or Absent with Hepatoma Plasma Membranes", *J. of Biochem.* 284:625–628 (1992).

Morré et al. "NADH Oxidase of Liver Plasma Membrane Stimulated by Diferric Transferrin and Neoplastic Transformation Induced by the Carcinogen 2–Acetylaminofluorene", *Biochimica et Biophysica Acta* 1057:140–146 (1991).

Morré and Crane, "Oxidoreduction at the Plasma Membrane: Relation to Growth and Transport" vol. I; Animals Eds. Crane, Morré and Löw (CRC Press, Boca Raton, FL), pp. 67–84 (1990).

Sun et al., "Requirement for Coenzyme Q in Plasma Membrane Electron Transport", *Prod. Natl. Acad. Sci. USA* 89:11126–11130 (1992).

Primary Examiner—Nathan M. Nutter
Attorney, Agent, or Firm—Bertram I. Rowland

[57] ABSTRACT

N-Acylated catecholmethylamines are used to inhibit cancer cell proliferation. Specifically, capsaicin is found to inhibit growth at low concentration, but not normal cells.

9 Claims, 4 Drawing Sheets

5,569,673

CAPSACINOID COMPOUNDS AS PROLIFERATION INHIBITORS

TECHNICAL FIELD

The field of this invention is the treatment of neoplasia.

BACKGROUND

Cancer has been one of the major plagues of society. Cancer appears to be a result of genetic defects, aging, viral infections, exposure to mutagens, and may have other causative events. The uncontrolled proliferation of non-functional cells can lead to rapid death or lingering illness. For the most part, approaches have depended upon the high proliferation of neoplastic cells as the basis for the therapy. Thus, many of the compounds are concerned with inhibiting DNA replication or causing dysfunctional replication resulting in cell death. However, neoplastic cells are not the only cells which are undergoing rapid proliferation in the body. Of particular moment are blood cells which are continuously being turned over through a highly orchestrated process emanating from a unique stem cell, which is able to differentiate into all of the different cellular pathways of the hematopoietic system, as well as providing a source for other cells, such as osteoclasts. Inhibition of the hematopoietic system results in the individual's susceptibility to opportunistic diseases, as well as adverse symptoms associated with aspects of the hematopoietic system not immediately directed to the immune system. Other tissues which require continuous replenishing include cutaneous tissue, hair follicles, linings of major organ systems, etc. Therefore, controlling cancer by inhibiting cell proliferation is problematical due to its adverse side effects.

Despite the extremely sophisticated tools which have been developed to identify genes associated with a particular phenotype, as yet, markers specific for neoplastic cells remain very rare. Morré et al. (1991) *Biochim. Biophys. Acta* 1057, 140–156; and Bruno et al. (1992) *Biochem. J.* 284, 625–628 reported an NADH oxidase activity which in cancer cells was constitutively activated and no longer hormone responsive.

The NADH oxidase activity appears to be associated with the ability of cells to proliferate. Inhibition of the enzyme results in a slowing of the proliferation of neoplastic cells. Since there appears to be a difference in the activity between the NADH oxidase of normal and neoplastic cells, there is substantial interest in being able to identify compounds which may selectively inhibit the NADH oxidase associated with neoplasia.

The NADH oxidase of petroleum ether-extracted plasma membranes is inhibited by certain quinone inhibitors. Sun et al. (1992) *Proc. Natl. Acad. Sci. USA* 89, 11126–11130. The involvement of NADH oxidase in the control of cell proliferation is described by Morré and Crane (1990) in *Oxidoreduction at the Plasma Membrane: Relation to Growth and Transport. I. Animals* Eds. Crane, Morré and Löw (CRC Press, Boca Raton, Fla.), pp. 67–84. The activity in transformed cells and tissues was distinguished from that of liver in that the growth factor- and hormone-responsiveness was lost in plasma membranes of liver tissues transformed with 2-acetylaminofluorene. Morré et al. (1991) *Biochim. Biophys. Acta* 1057, 140–156. The same loss of responsiveness was observed with transplanted rat hepatomas. Bruno et al. (1992) *Biochem,. J.* 284, 625–628.

SUMMARY OF THE INVENTION

N-Acylated catecholmethylamines, particularly the monomethyl ether, are used as inhibitors of NADH oxidase activity associated with neoplastic cells. The at least partially purified compounds are administered to a cell population suspected of having or resulting in neoplastic cells in an amount sufficient to substantially diminish the rate of proliferation of the neoplastic cells. The cell population may be a tumor in a mammalian host where administration is in a physiologically acceptable formulation to the host suspected of having neoplasia. Of particular interest are capsacinoids, where the fatty acid acyl group may be varied as to length, branching and degree of unsaturation, or their conjugates.

DESCRIPTION OF SPECIFIC EMBODIMENTS

Figure 1:
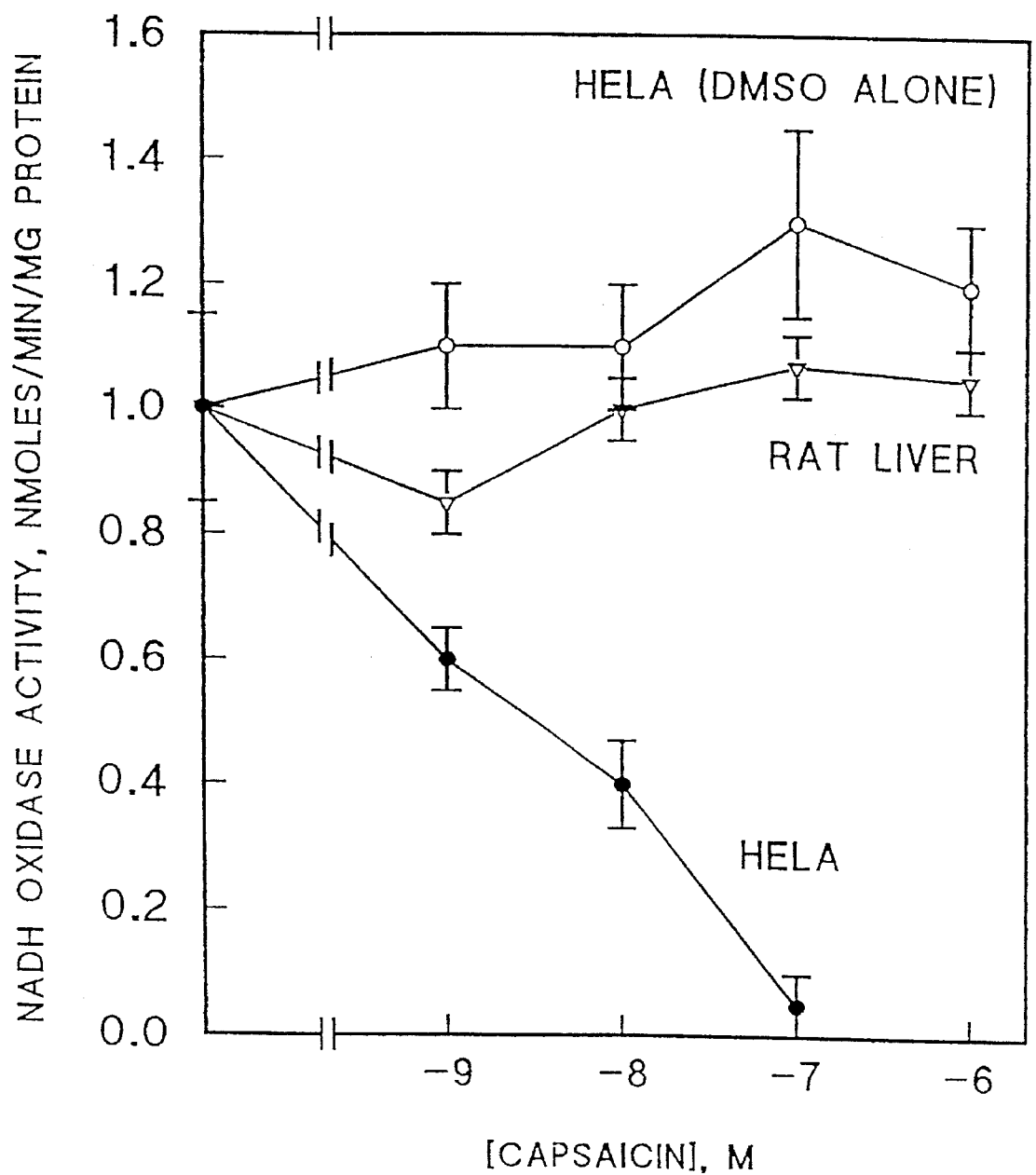
FIG. 1 is graph of the dose response of NADH oxidase of HeLa cell plasma membranes to capsaicin in DMSO (solid circles) or an equivalent amount of DMSO alone (open circles). The response of rat liver plasma membrane vesicles to capsaicin is shown by the open triangles. Values are duplicate determinations plus/minus mean average deviations.

Lipophilic fatty acid amides of catecholmethylamines are employed for inhibiting the rate of proliferation of neoplastic cells. The target is believed to be NADH oxidase, a surface membrane protein amenable to being used as a target with impermeant drugs (drugs which need not enter the cytoplasm to exert their activity), where the NADH oxidase activity can be distinguished between normal and neoplastic cells, based on the response to a number of different agents. Of particular interest are fatty acid amides of vanillylmethylamines, where the fatty acids are aliphatic of at least 6 carbon atoms, and may be aliphatically saturated or unsaturated. The compositions may be used to prevent overgrowth by neoplastic cells in a cell population in culture or in vivo, by contacting the cells with neoplastic cell derived NADH oxidase inhibiting amount of one or a combination of the subject compounds. The compositions may be formulated in physiologically acceptable formulations for oral or parenteral administration to provide an effective dosage at the tumor site to reduce the rate of cellular proliferation.

Generically, the subject compounds may be considered as fatty acid amides of physiologically acceptable aliphatic carboxylic acids and a catecholmethylamine, more particularly, where one of the hydroxy groups is alkylated with an alkyl group of from 1 to 3, preferably 1 carbon atom, i.e. methyl, and the substitution on the ring is 1-aminomethyl-3,4-dihydroxy, where particularly the 3-hydroxy is alkylated.

The fatty acids which acylate the amine will generally be of at least 6 carbon atoms, more usually of at least about 8 carbon atoms, and not more than about 26 carbon atoms, usually not more than about 24 carbon atoms, preferably from about 8 to 18 carbon atoms, more preferably from about 8 to 11 carbon atoms. The aliphatic carboxylic acids may be straight or branched chain, particularly branched at the penultimate carbon atom ($\Omega$-1) (isoalkanoic acids or unsaturated analogs thereof), where the branch will usually be of from 1 to 2 carbon atoms, more usually of 1 carbon atom. Unsaturation may be ethylenic or acetylenic (double or triple bond) where the unsaturation may be at any site in the chain, particularly $\Omega$-4–$\Omega$-2, where $\Omega$-4 intends unsaturation between $\Omega$-4 and $\Omega$-3, that is between the third and fourth carbon atoms counting from the last carbon atom as one. Fatty acids which may find use include 9-methyldec-7-enoic acid, 9-methyloct-6-enoic acid, lauric acid, caproic acid, oleic acid, stearic acid, palmitic acid, myristic acid, octanoic acid, palmitoleic acids, linoleic acid, arachidonic acid, and the acids naturally found with the vanillyl methyl amine as the active component of chili peppers.

The subject compounds will be used in at least partially purified form, usually comprising at least 20 weight %, more usually at least about 50 weight %, conventionally at least about 90 weight % and up to 100 weight % of the subject compounds in a composition for formulation or addition to a culture or other medium.

The subject compositions may be used for treating any vertebrate host which may have or may be subject to transformation of cells resulting in neoplasia. Thus, the subject compositions may be used with mammals, particularly primates, more particularly humans, fish, birds, etc. The subject compositions may be used prophylactically, where due to environmental stresses, work, genetic predisposition, accidents or other transforming stimuli, a mammalian host may have an increased propensity for tumor formation. By providing a prophylactic regimen of the subject compounds, the probability of forming cancers dependent on the tumor form of NADH oxidase may be substantially diminished.

The subject compositions may be used with any tumorous condition which expresses the aberrant NADH oxidase, including carcinomas, melanomas, sarcomas, leukemias, lymphomas, etc., where the tissues involved may be the prostate, mammary, neuronal, testes, lung, cutaneous tissue, lymph node, mucosal tissue, muscle tissue, lymphocytes, ovary, glandular, e.g. pancreas, and the like. The subject compositions may be used with hyperproliferative tissue, e.g. precancerous but neoplastic lesions, a single tumor, or metastatic tumors.

The response of the neoplastic cells to the subject compositions may be monitored by assaying the blood of the patient for NADH oxidase which is responsive to the subject treatment. Various assays may be used for determining whether the NADH oxidase present in the tumor cells is different from the NADH oxidase of normal cells. See, for example, U.S. application Ser. No. 08/222,799, filed Apr. 5, 1994. Differential response to other anticancer drugs, e.g. adriamycin, may be used, where the $ED_{50}$ for NADH oxidase from neoplastic cells is about 0.7 nM, approximately 1000 fold less than for NADH oxidase from normal cells. The inhibition can be observed by following the rate of change in concentration of NADH or NAD, in accordance with known procedures.

An effective dosage of the subject compositions may be administered in accordance with the need of the particular patient. Because of the low toxicity of the subject compounds to normal cells, the subject compositions may be repeatedly administered over various intervals. Usually, the accumulated dosage per treatment cycle will be in the range of about 1 mg to 100 mg/kg of body weight, depending upon the efficacy of the particular formulation, the site of administration, the manner of administration, the tumor of origin and the disease stage. Treatment cycles will be repeated as necessary.

The subject drugs may be administered singly or in combination with other drugs of the same family. The subject drugs will usually be administered in a physiologically acceptable vehicle, such as saline, PBS, water, aqueous ethanol, vegetable oil, glycerol, 25% dimethyl sulfoxide, etc. The concentration of the subject compositions will generally be in the range of about 0.003 to 1% for topically applied creams and salves or ointments, and 1 to 100 mg/ml for other routes, where the amount will vary with the frequency of administration, the nature of the administration, the nature of the tumor, and the like.

Depending on the nature of the tumor, administration may be orally, parenterally, such as intravascularly, intragastrically, subcutaneously, intraperitoneally, intralesionally, or topically, or the like. The frequency of administration may be with intervals of 4 hours, 1 day, 3 days, 1 week, 1 month or more, depending upon the need of the patient. The particular regimen will be determined empirically, in accordance with the indication, the response to the therapy, and the like.

The subject compounds may be modified by providing for a functional group on the fatty acid, particularly the terminal carbon atom of the fatty acid. Since the compositions may be readily prepared by acylating the catecholmethylamine, any acylating group may be used which has the appropriate biological and chemical activity. One can use the functional site for conjugation to another compound to enhance the specificity of the subject compounds for neoplastic cells. For example, one may covalently bond the subject compounds with diferric transferrin or other impermeant drug, since the target protein is at the cell surface with a resultant cancer agent having enhanced selectivity and specificity. Alternatively, one may conjugate the subject compounds to growth factors, hormones or antibodies which have enhanced specificity for one or more cell or organ types. For example, with estrogen dependent breast cancers, one could couple the subject compound to an estrogen. For T cell leukemias, one would link the subject compounds to an appropriate cytokine, a major histocompatibility antigen which restricts the T cell, or the like. Instead of covalent bonding, one could use non-covalent association, such as through complex formation, e.g. lectin-sugar, antibody-ligand, etc., membrane association, with the formation of liposomes having the two compounds on the surface of the liposome, or the like.

To further enhance the therapy, one may use consecutively or concurrently with the subject compounds, growth factors or hormones which enhance the efficacy of the subject compounds as growth inhibitors. By growth factors is intended any of the substances normally capable of interacting with surface receptors to alter cell responses, such as epidermal, platelet-derived, diferric transferrin, lactoferrin, bombesin, glucagon, insulin, epinephrine, and the like. Alternatively, one may use oxidants and reductants, including, but not limited to ascorbic acid, dehydroascorbic acid, glutathione, dithiothreitol, N-acetyl cysteine, cysteine, etc. These compounds would be used in their normal therapeutic range or their dosage be determined empirically in accordance with known procedures. In view of their safe nature, a wide dynamic range is permissible.

In many instances, it may be desirable to use combination therapies, where the subject compositions may be used in conjunction with other known drugs. Drugs which may be used in combination include conventional drugs, such as alkylating agents, e.g. carmustine, antimetabolites e.g. 5-fluorouracil antibiotics, e.g. adriamycin, bleomycin, and daunomycin, alkaloids, e.g. vinblastine, biological modifiers, e.g. taxol, biological response modifiers, e.g. interleukins, and other agents, e.g. cis-platinum, and the like.

In many cell populations, one may wish to grow normal cells in the substantial absence of neoplastic or other aberrant cells. Where the aberrant cells express the NADH oxidase associated with neoplastic cells, a growth inhibiting amount of the subject compositions may be used in the growth medium. The concentration of the subject compositions in the medium will usually be at least about 10 nM and not more than about 500 nM, more usually in the range of about 50 to 250 nM. In this way cell populations may be expanded or maintained in culture for various time periods, while preventing the growth of neoplastic cells.

The use of the subject compounds may find application with transplants which are maintained in culture prior to being administered to a recipient mammalian host. Thus, the subject compounds may be used with bone marrow, organs, blood, and the like. In addition, for research purposes where cells are established in culture for use in studying cellular growth and proliferation, changes in metabolic response to various compounds or stimuli, maintenance at a primitive level, or the like, the overgrowth with neoplastic cells can be prevented by use of the subject compounds in the media.

The subject compounds may also be used to direct various compositions to neoplastic cells. By using the subject compounds as markers on liposomes, where cytotoxic drugs are included in the lumen of the liposome, the liposomes may be preferentially directed to neoplastic cells. The subject compositions may be provided with the acyl group of at least about 12 carbon atoms, so as to be included in the liposome membrane, or the terminal carbon atom of the acyl group may be functionalized with an hydroxyl or amino group, in accordance with known ways and the functional group acylated with a fatty acid of at least about 12 carbon atoms, particularly 14 to 30 carbon atoms.

Liposomes may be made in accordance with conventional ways, using the subject compositions as one of the lipids. By combining cholesterol, phosphatidyl choline, acyl glycerols, and the like with an aqueous solution of one or more drugs of interest and vigorously agitating the mixture, liposomes may be formed, where the liposome membrane will comprise the subject compositions, which will preferentially bind to neoplastic cell associated NADH oxidase.

The subject compositions may also be used in competitive immunoassays, where a subject compound is conjugated to a haptenic analyte of interest. The conjugation may be carried out in accordance with known ways, where the acyl group is functionalized as described above. The conjugate may compete with analyte in an assay medium comprising the neoplastic cell associated NADH oxidase for antibody to the haptenic analyte. The amount of antibody which binds to the conjugate will be proportional to the amount of hapten in the assay medium. The conjugate will inhibit the NADH oxidase enzyme when unbound and be prevented from inhibiting the enzyme when bound to antibody. Therefore, the enzyme activity can be related to the amount of haptenic analyte in the assay medium. See, particularly U.S. Pat. No. 3,935,074.

The following examples are offered by way of illustration and not by way of limitation.

EXPERIMENTAL

Methods of Procedure

Growth of cells.

HeLa cells (ATCC CCL2), were grown in 150 cm$^2$ flasks in Minimal Essential Medium (Gibco), pH 7.4. at 37° C. with 10% bovine calf serum (heat-inactivated), plus 50 mg/l gentamycin sulfate (Sigma). Cells were trypsinized with Sigma IX trypsin for 1 to 2 min, harvested by scraping and taken up in TD-tris buffer (140 mM NaCl, 5 mM KCl, 0.7 mM Na$_2$HPO$_4$ and 25 mM Tris, pH 7.4) to a final cell concentration of 0.1 g wet weight (gww) per ml.

Purification of plasma membranes from rat liver.

The 5000×g pellet from the preparation of Golgi apparatus (Morré (1971) *Meth. Enzymol.* 22, 130–148) was the starting material. The fluffy layer which contains the Golgi apparatus fraction was mixed, withdrawn and excluded from the plasma membrane preparations. Cold 1 mM NaHCO$_3$ (5 ml) was added to each tube and the friable yellow-brown upper part of the pellet was resuspended with a pen-brush, leaving the reddish tightly packed bottom part of the pellet undisturbed. The resuspended material was homogenized in aliquots of 5 ml each in a 30 ml stainless steel homogenizer (Duragrind) 20 times by hand. The homogenates were combined, diluted with cold 1 mM NaHCO$_3$ (1:1 dilution), and centrifuged at 6000×g in a HB rotor for 15 min. The supernatant was discarded and the pellet was used for the two-phase separation (Morré & Morré (1989) *BioTechniques* 7: 946–958).

The two-phase system contained 6.4% (w/w) Dextran T-500 (Pharmacia), 6.4% (w/w)polyethylene glycol) 3350 (Fisher), and 5 mM potassium phosphate buffer (pH 7.2) (Morré & Morré, 1989, supra). The homogenate (1 g) was added to the two-phase system and the weight of the system was brought to 8 g with distilled water. The tubes were inverted vigorously for 40 times in the cold (4° C.). The phases were separated by centrifugation at 750 rpm (150×g) in a Sorvall HB 4 rotor for 5 min. The upper phases were carefully withdrawn with a pasteur pipette, divided in half and transferred into 40 ml plastic centrifuge robes and diluted with cold 1 mM NaHCO$_3$. The purified plasma membranes were collected by centrifugation at 10,000×g in a HB rotor for 30 min. Plasma membrane pellets were resuspended in 50 mM Tris-Mes buffer (pH 7.2) and stored at −70° C. Proteins were determined using the bicinchoninic acid (BCA) assay (Smith et al. (1985) *Anal. Biochem.* 100: 76–85) with bovine serum albumin as standard. Yields were approximately 3–5 mg per 10 g liver (Navas et al. (1989) *Cancer Res.* 49: 2146–2147).

The plasma membrane preparations from rat liver have been characterized extensively based on both morphological and enzymatic criteria (Morré (1971) supra; Smith et al. (1985) supra). From morphometric analysis using electron microscopy, the preparations contain 90±4 percent plasma membrane. Contaminants include mitochondria (4%) and endoplasmic reticulum (3%). Based on analyses of marker enzymes, the contamination by endoplasmic reticulum was estimated to be 3%, that of mitochondria 15% and that of Golgi apparatus 1%. The recovery of plasma membranes was estimated to average 18% based on recovery of enzyme markers.

Purification of plasma membranes from HeLa cells.

HeLa cells were grown as suspension cultures in minimum essential medium (MEM) supplemented with horse serum, diferric transferrin and heparin. Cells were collected by centrifugation for 6 to 15 min at 1,000 to 3,000 rpm. The cell pellets were resuspended in 0.2 mM EDTA in 1 mM NaHCO$_3$ in an approximate ratio of 1 ml per $10^8$ cells and incubated on ice for 10 to 30 min to swell the cells. Homogenization was with a Polytron Homogenizer for 30 to 40 sec at 10,500 rpm using a PT-PA 3012/23 or ST-probe in 7 to 8 ml aliquots. To estimate breakage, the cells are monitored by light microscopy before and after homogenization. At least 90% cell breakage without breakage of nuclei was achieved routinely.

The homogenates were centrifuged for 10 min at 1,000 rpm (175 g) to remove unbroken cells and nuclei and the supernatant was centrifuged a second time at $1.4 \times 10^6$ g min (e.g. 1 h at 23,500 g) to prepare a plasma membrane enriched microsome fraction. The supernatant was discarded and the pellets were resuspended in 0.2M potassium phosphate buffer in a ratio of approximately 1 ml per pellet from $5 \times 10^8$ cells. The resuspended membranes were then loaded onto the two-phase system constituted on a weight basis as described above for rat liver. The upper phase, enriched in plasma membranes, was diluted 5-fold with 1 mM sodium bicarbonate and the membranes were collected by centrifugation. The purity of the plasma membrane was determined to be >90% by electron microscope morphometry. The yield was 20 mg plasma membrane protein from $10^{10}$ cells.

Spectrophotometric assay of NADH oxidase.

NADH oxidase activity was determined as the disappearance of NADH measured at 340 nm in a reaction mixture containing 25 mM Tris-Mes buffer (pH 7.2), 1 mM KCN to inhibit the low levels of contaminating mitochondrial oxidase activity, and 150 μM NADH at 37° C. with constant stirring. Activity was measured using a Hitachi U3210 spectrophotometer with continuous recording over two intervals of 5 min each. A millimolar extinction coefficient of 6.22 was used to determine specific activity.

EXAMPLES

Capsaicin was without effect on the NADH oxidase of plasma membranes from rat liver (FIG. 1). However, with plasma membrane from HeLa cells, the activity was inhibited by capsaicin with an ED$_{50}$ of about 50 nM (FIG. 1). At 0.1 μM capsaicin, the activity was nearly completely inhibited.

In addition to inhibition of NADH oxidase of plasma membranes, capsaicin also inhibited the growth of attached HeLa cells in culture. Inhibition of growth of attached HeLa cells during 72 h of culture by capsaicin under normal conditions of cell culture was observed. The number of cells initially plated was subtracted. The results were averages from duplicate experiments. Growth was 50% inhibited at about 1 μM. However, with attached HeLa cells where the growth factor conditions were manipulated to increase drug efficacy, growth was inhibited completely at a concentration of capsaicin of 10 to 100 nM. This result correlated closely with the inhibition of NADH oxidase activity of the HeLa cell plasma membranes (FIG. 1).

Figure 2:
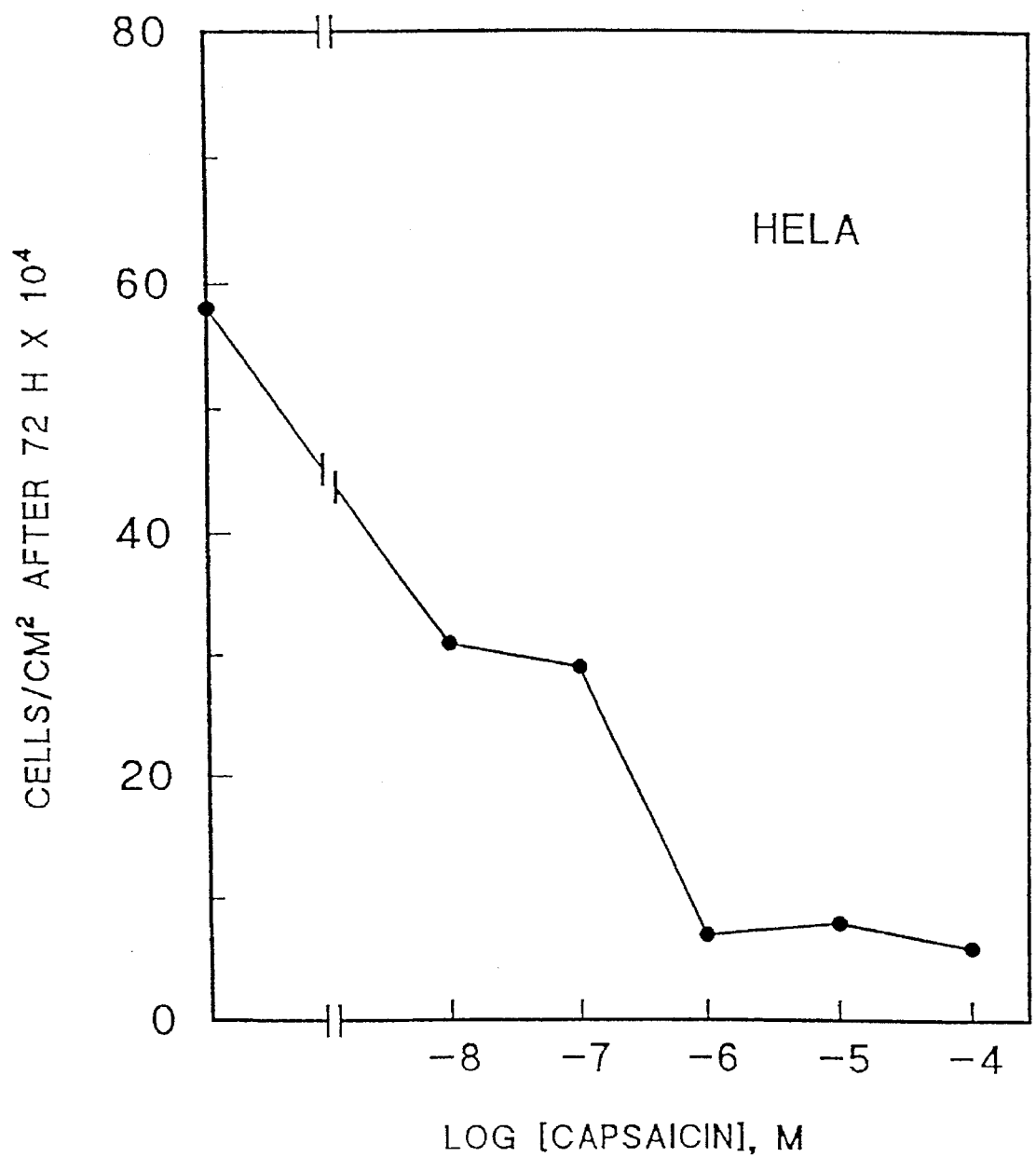
FIG. 2 is a graph of the growth of HL-60 cells with time as a function of capsaicin concentration. The inset shows the growth response of HL-60 cells induced to differentiate with DMSO determined in parallel. The concentrations refer to final concentrations present in the medium.

HL-60 cells grown in suspension were inhibited as well by capsaicin (FIG. 2). However if the cells were induced to differentiate with DMSO, the cells became resistant to the inhibitory effects of capsaicin (FIG. 2, inset). If after several days following the DMSO-induced differentiation, the cells resumed rapid growth, the capsaicin once again inhibited the growth.

With the HL-60 cells, the NADH oxidase activity of isolated plasma membranes was inhibited as well by cap-saicin. However, with plasma membranes isolated from cells freshly induced with DMSO, the NADH oxidase activity appeared to resist inhibition by capsaicin.

Figure 3:
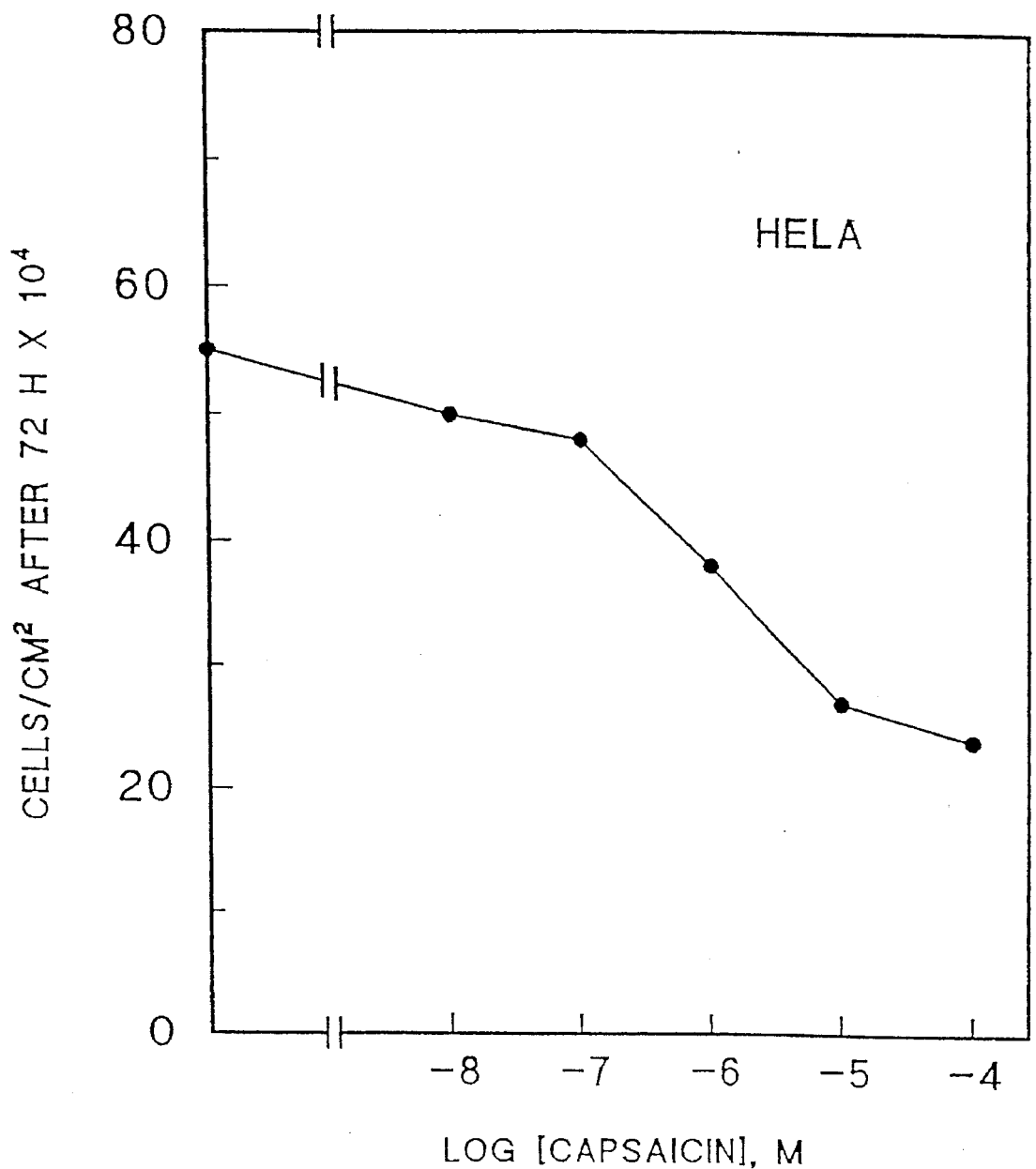
FIG. 3 is a graph of the growth of normal rat kidney (NRK) cells as a function of capsaicin concentration over 48 and 96 h of treatment.
Figure 4:
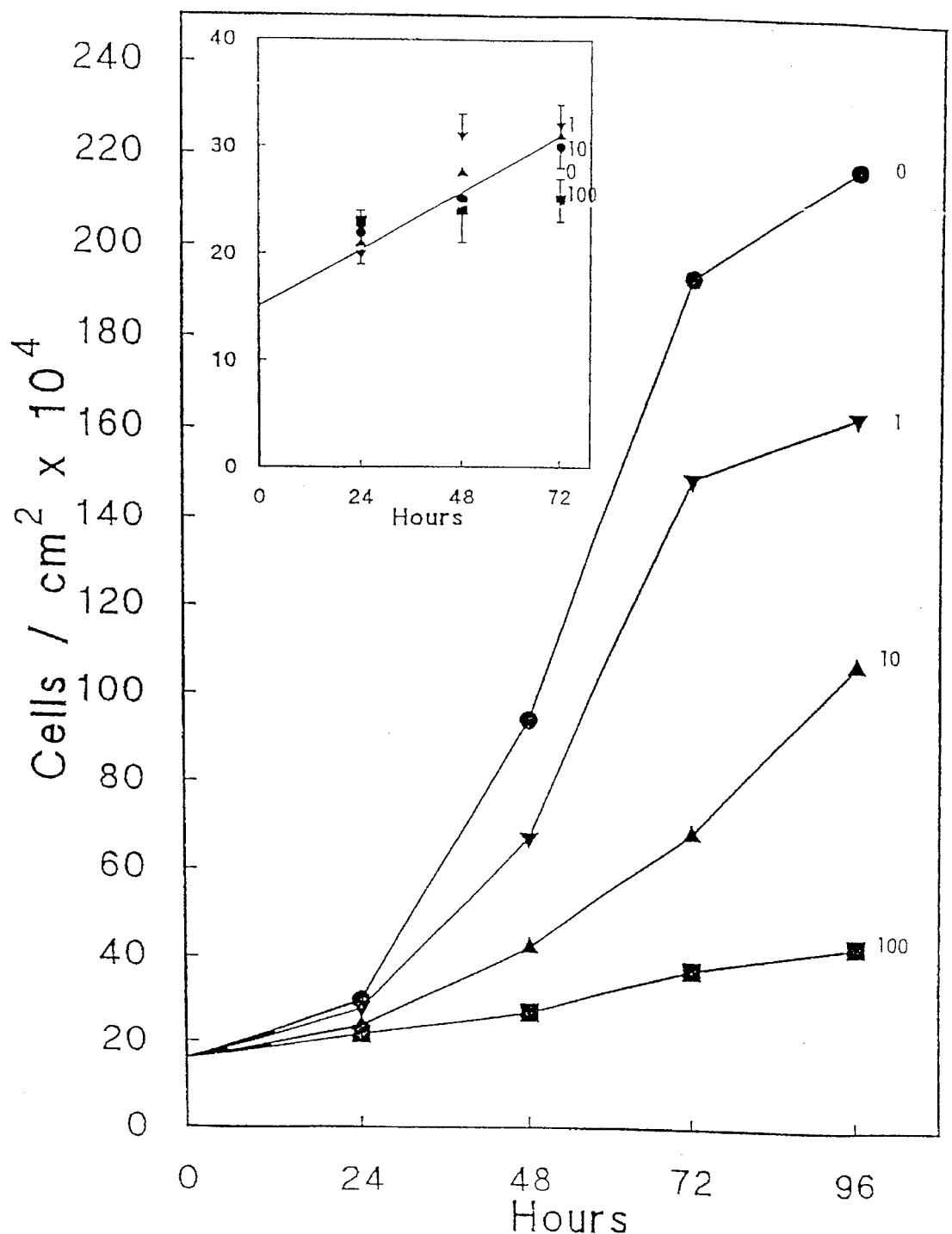
FIG. 4 is a graph of the NADH oxidase activity of plasma membrane vesicles isolated from NRK cells as a function of the concentration of capsaicin (in DMSO) compared to DMSO alone.

As an example of a non-cancer cell type, the growth and NADH oxidase activity of normal rat kidney cells were examined. Neither growth (FIG. 3) nor NADH oxidase activity of isolated plasma membranes compared to DMSO alone (FIG. 4) was inhibited by capsaicin except at very high concentrations (>$10^{-5}$M).

The above results support the conclusion that NADH oxidase activity of HeLa cells (human ovarian carcinoma derivation) are inhibited by capsaicin. In contrast to the observation with HeLa plasma membranes, plasma membranes of normal cells from rat liver or rat kidney were not inhibited. Similarly, the NADH oxidase of HL-60 (human leukemia cells) was inhibited by capsaicin, but upon induction or differentiation with DMSO (Collin et al. (1979) *J. Exp. Medicine* 14: 969–974), the NADH oxidase activity of the isolated plasma membrane vesicles was much less inhibited.

Not only does capsaicin inhibit the NADH oxidase of plasma membrane vesicles from cancer cells anti not from normal cells, the substance exerts a parallel response on growth. Growth is nearly completely inhibited by capsaicin with HeLa and HL-60 cells where rat kidney and HL-60 cells induced to differentiate with DMSO are substantially less affected by the capsaicin.

The effect of capsaicin, which is representative of a group of pungent principals from chile peppers, may be correlated with the observation that there is an inverse ratio between cancer death rates and diets traditionally high in chile peppers. Compared to the United States, cancer death rates at all sites were 157 for males and 106 for females compared to 56 and 71 for Mexico and 29 and 20 for Thailand (the lowest of any country). The capsaicin need not be pure to be active. Extracts derived from jalapeña peppers at dilutions of 1:100 and 1:1000 inhibit activity of NADH oxidase of plasma membrane vesicles prepared from HeLa cells.

TABLE 1

Response of NADH oxidase activity of HeLa plasma membrane vesicles to an extract (Mashate prepared with no additions) from fresh pericarp of jalapeña peppers tested at dilutions of 1:100 and 1:1000.

|  | nmoles/min/mg protein |
| --- | --- |
| Control + Extract 1:1000 | 0.9 |
|  | 0.5 |
|  | Δ-0.4 |
| Control + Extract 1:100 | 1.0 |
|  | 0.2 |
|  | Δ-0.8 |

Comparing sera of 11 normal individuals, capsaicin was without effect at 100 nM. With sera from 12 cancer patients, activity was inhibited with 9 and stimulated with 3. The results are reported in the following table.

TABLE 2

NADH oxidase activities of human serum in response to 100 nM capsaicin.

|  | None | 100 nM capsaicin | Ratio |
| --- | --- | --- | --- |
| SB-69 Bladder | 0.3 | 0.2 | 0.66 |
| SB-11 Renal cell | 0.6 | 0.45 | 0.75 |

TABLE 2-continued

NADH oxidase activities of human serum in response to 100 nM capsaicin.

|  | None | 100 nM capsaicin | Ratio |
|---|---|---|---|
| SB-4 Prostate | 0.45 | 0.2 | 0.44 |
| SB-58 Bladder | 0.9 | 0.45 | 0.5 |
| SB-76 CML | 1.8 | 1.5 | 0.8 |
| SB-74 Small lung cell | 0.8 | 1.0 | 1.25 |
| SB-65 Lymphoma | 0.6 | 0.9 | 1.5 |
| SB-68 Leukemia | 0.65 | 0.75 | 1.15 |
| SB-77 Colon | 0.9 | 0.6 | 0.66 |
| SB-66 Breast | 0.8 | 0.6 | 0.75 |
| SB-65 Lymphoma | 0.25 | 0.15 | 0.6 |
| SB-72 Lung | 0.6 | 0.4 | 0.66 |
| PU-21 | 0.45 | 0.45 | 1.0 |
| PU-10 | 0.45 | 0.45 | 1.0 |
| PU-25 | 0.6 | 0.53 | 0.9 |
| PU-24 | 0.25 | 0.25 | 1.0 |
| PU-21 | 0.2 | 0.2 | 1.0 |
| PU-22 | 0.6 | 0.625 | 1.04 |
| PU-27 | 1.1 | 1.05 | 0.95 |
| PU-31 | 0.475 | 0.45 | 0.95 |
| PU-29 | 0.825 | 0.8 | 0.97 |
| PU-28 | 0.275 | 0.275 | 1.0 |
| PU-30 | 1.1 | 1.1 | 1.0 |
| Mean | 0.575 | 0.56 | 0.97 |

It is evident from the above results that the subject compositions have a preferential effect in inhibiting growth of tumor cells, while having substantially no effect on normal cell growth. The patient may be monitored for response to the use of the subject compounds by determining the response of the NADH oxidase in the bloodstream. In this way, patients may be conveniently screened for determining their response to the subject therapy. The subject compounds are safe, being naturally occurring substances or analogous thereto, can be used at elevated concentrations with few side effects and do not require transport across the membrane for activity. In addition, the subject compositions can be readily administered in a wide variety of ways, while retaining efficacy. By employing the subject therapy, one can achieve reduction of tumor proliferation, so as to reduce the tumor burden, to allow other therapies to be used, which might otherwise be unacceptable, due to adverse side effects. In addition, the subject therapies do not interfere with the host immune system, but allow for cooperation with the proliferation inhibition of the subject compounds and the cytotoxic activity of the immune system.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for inhibiting proliferation of neoplastic cells, said method comprising administering to a cell population suspected of comprising neoplastic cells, a proliferation inhibiting amount of a purified N-acylated catecholmethylamine inhibitor of NADH oxidase of neoplastic cells, wherein said acyl group is from 6 to 26 carbon atoms, whereby proliferation of neoplastic cells is inhibited.

2. A method according to claim 1, wherein said catecholmethylamine is a capsacinoid.

3. A method according to claim 2, wherein said capsacinoid is capsaicin.

4. A method according to claim 2, wherein a capsacinoid is administered in combination with a chemotherapeutic drug other than said capsacinoid.

5. A method for inhibiting proliferation of neoplastic cells in a mammalian host, said method comprising:

assaying a blood sample of said host for NADH oxidase which is hormone unresponsive and capsacinoid responsive; and administering to a host positive for said NADH oxidase a neoplastic cell inhibiting amount of a purified capsacinoid in a physiologically acceptable formulation.

6. A method according to claim 5, wherein said capsacinoid is capsaicin.

7. A method according to claim 5, wherein a chemotherapeutic drug other than said capsacinoid is administered in combination with said capsacinoid.

8. A method for inhibiting proliferation of neoplastic cells in a mammalian host, said method comprising:

administering intralesionally into tumor cells, expressing an NADH oxidase which is hormone unresponsive and capsacinoid responsive, in a physiologically acceptable medium an NADH oxidase inhibiting amount of a capsacinoid.

9. A method for inhibiting proliferation of neoplastic cells in a mammalian host, said method comprising:

administering intravascularly, into a host comprising tumor cells expressing an NADH oxidase which is hormone unresponsive and capsacinoid responsive, in a physiologically acceptable medium an NADH oxidase inhibiting amount of a capsacinoid.

* * * * *